(12) United States Patent
Schneider et al.

(10) Patent No.: US 7,696,123 B2
(45) Date of Patent: Apr. 13, 2010

(54) DIMERIZATION CATALYST SYSTEMS, THEIR PREPARATION, AND USE

(75) Inventors: Katharina J. Schneider, Bruckmuhl (DE); Alt G. Helmut, Bayreuth (DE); George D. Parks, Bartlesville, OK (US); Roland Schmidt, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 579 days.

(21) Appl. No.: 11/542,945

(22) Filed: Oct. 4, 2006

(65) Prior Publication Data

US 2008/0085829 A1 Apr. 10, 2008

(51) Int. Cl.
*B01J 37/00* (2006.01)
*C08F 4/02* (2006.01)

(52) U.S. Cl. .................. 502/117; 502/102; 502/104; 502/110; 502/111

(58) Field of Classification Search .......... 502/102, 502/104, 110, 111, 117; 585/513, 514, 528, 585/531, 532, 533
See application file for complete search history.

(56) References Cited

U.S. PATENT DOCUMENTS

| | | | | |
|---|---|---|---|---|
| 3,992,323 A | * | 11/1976 | Yoo et al. .................... | 502/117 |
| 4,709,112 A | * | 11/1987 | Sato et al. ................... | 585/513 |
| 5,932,670 A | | 8/1999 | Koppl et al. ................ | 526/161 |
| 5,990,035 A | * | 11/1999 | Koppl et al. ................ | 502/152 |
| 6,159,888 A | | 12/2000 | Welch et al. ................ | 502/117 |
| 6,162,884 A | | 12/2000 | Alt et al. ..................... | 526/161 |
| 6,262,201 B1 | | 7/2001 | Welch et al. ................ | 526/127 |
| 6,329,312 B1 | | 12/2001 | Licht et al. .................. | 502/117 |
| 6,458,905 B1 | | 10/2002 | Schmidt et al. ............. | 526/172 |
| 6,531,554 B2 | | 3/2003 | Alt et al. ..................... | 526/160 |
| 2002/0039960 A1 | | 4/2002 | Alt et al. ..................... | 502/117 |
| 2003/0144438 A1 | | 7/2003 | Schmidt et al. ............. | 526/172 |

FOREIGN PATENT DOCUMENTS

| | | |
|---|---|---|
| EP | 1 402 949 A1 | 3/2004 |
| WO | WO 03/102038 A1 | 12/2003 |

OTHER PUBLICATIONS

Carlini et al., "Ethylene oligomerization by novel catalysts based on bis (salicylaldiminate) nickel (II) complexes and organoaluminum co-catalysts," Applied Catalysis A: General 231 (2002) pp. 307-320.
Carlini et al., "Ethylene Polymerization by Bis (salicylaldiminate) nickel (II)/Aluminoxane Catalysts," published online in Wiley InterScience (www.interscience.wiley.com), accepted Jan. 21, 2004, pp. 2534-2542.
Carlini et al., "Ethylene homopolymerization by novel Ziegler Natta-type catalytic systems obtained by oxidative addition of salicylaldimine ligands to bis (1,5-cyclooctadiene) nickel (0) and methylalumoxane," Polymer 44 (2003), pp. 1995-2003.
Sauthier et al., "NiCl$_2$ (1,2-Diiminophosphorane) complexes; a new family of readily accessible and tuneable catalysts for oligerimisation of ethylene," New J. Chem., 2002, 26, pp. 630-635.

* cited by examiner

*Primary Examiner*—In Suk Bullock

(57) ABSTRACT

A method for preparing a nickel-containing composition, and a composition prepared by such method, are disclosed including the steps of: a) mixing a phosphorous compound with a nickel complex having nickel bonded to a heteroatom to thereby form a nickel-phosphorous-containing mixture; and b) contacting the nickel-phosphorous-containing mixture with a supported partially hydrolyzed alkylaluminum compound, thereby forming such nickel-containing composition. Use of such nickel-containing composition in the dimerization of propene is also disclosed.

11 Claims, No Drawings

DIMERIZATION CATALYST SYSTEMS, THEIR PREPARATION, AND USE

This invention relates to catalyst systems useful for dimerization of propene.

Propene dimerization can produce certain hexenes which have high octane numbers (such as 2, 2 or 2, 3 dimethylbutene). The hydrogenation products of these hexenes can make excellent blend stocks for the gasoline pool, improving the overall octane rating.

DETAILED DESCRIPTION OF THE INVENTION

In one embodiment of the invention, a method for producing a nickel-containing composition is provided.

Such method comprises:

a) mixing a phosphorous compound with a nickel complex comprising nickel bonded to a heteroatom, to thereby form a nickel-phosphorous-containing mixture; and b) contacting the nickel-phosphorus-containing mixture with a supported partially hydrolyzed alkylaluminum compound, thereby forming a nickel-containing composition.

The heteroatom is preferably selected from the group consisting of oxygen, nitrogen, sulfur, phosphorus, boron, and combinations thereof.

The nickel complex can comprise at least one compound having one of the following structures:

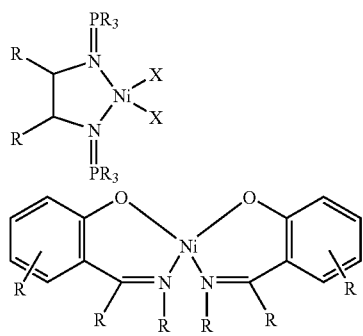

wherein:

R is selected from alkyl, aryl, alkenyl, hydrogen, and combinations thereof, any of which optionally can be partially oxidized or partially substituted by nitrogen-functional groups having the general formulas OH, OR and $NH_yR_z$, respectively;

X is a halogen atom;

y=3−z; and z ranges from 1 to 3.

The halogen X is preferably selected from the group consisting of chlorine and bromine.

The most preferred nickel complexes are those having the following formulas:

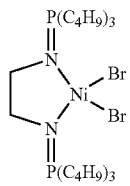

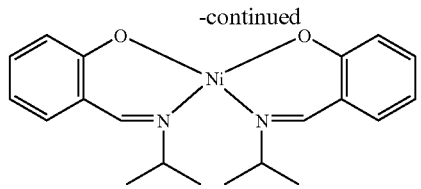

The phosphorous compound can be any phosphorous containing compound capable of being mixed with the nickel complex. Preferably, the phosphorous compound has the formula $R_nPY_{3-n}$;

wherein:

R is selected from alkyl, aryl, alkenyl, hydrogen, and combinations thereof, any of which optionally can be partially oxidized or partially substituted by nitrogen-functional groups having the general formulas OH, OR and $NH_yR_z$, respectively;

Y is selected from hydrogen and halogen;

y=3−z;

z ranges from 1 to 3, and n ranges from 1 to 3.

The phosphorous compound is more preferably selected from the group consisting of tributyl phosphine, triphenyl phosphine, triisopropyl phosphine, and combinations thereof.

Preferably, the supported partially hydrolyzed alkylaluminum compound is supported partially hydrolyzed trimethylaluminum. In addition, the support of the supported partially hydrolyzed alkylaluminum compound is preferably silica.

The conditions at which the inventive method is performed include a temperature in the range of from about −20° C. to about 150° C.

A solvent can also be used in step a) to aid in mixing the compounds; and removed in step b) to thereby form the nickel-containing composition. The solvent is preferably a hydrocarbon and is most preferably toluene.

The most preferred method is to add the nickel complex and the phosphorous compound to toluene, in either order, and then add the resulting mixture to the supported partially hydrolyzed alkylaluminum compound.

Supported partially hydrolyzed alkylaluminum compounds can be prepared by mixing a support with an alkylaluminum compound in the presence of a hydrocarbon solvent. The resulting mixture is then contacted with water vapor, forming the supported partially hydrolyzed alkyl aluminum compound. The support can be silica, alumina, or combinations thereof, and the hydrocarbon solvent is preferably toluene.

The resulting slurry is then filtered and rinsed with a paraffin such as isopentane and dried in vacuo. All steps are preferably carried out in an inert atmosphere, such as a nitrogen atmosphere.

In accordance with a second embodiment of the invention, a feedstream comprising propene is contacted with a nickel-containing composition prepared by the inventive method described above to convert at least a portion of the propene in the feedstream to hexenes. Preferably, at least 60 wt. % of the propene is converted to hexenes.

Such feedstream is contacted with the nickel-containing composition at a temperature in the range of from about −20° C. to about 150° C., preferably from about 20° C. to about 60° C., and at a pressure in the range of from about 40 psi to about 2000 psi, preferably from about 150 psi to about 350 psi, respectively.

The hexenes produced in the inventive process preferably comprise at least 30 wt. % dimethylbutenes.

The compositions prepared by the above described method form another embodiment of this invention.

EXAMPLES

Supported partially hydrolyzed trimethylaluminum was prepared by mixing silica and trimethylaluminum in toluene. Water vapor was then contacted with the mixture forming what is commonly known as PHT.

Example I

Separate quantities of the following diiminophosphorane Ni(II) complex having the formula:

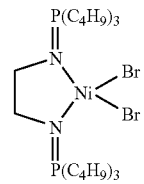

were mixed with either triphenyl phosphine (PPh$_3$) or triisopropyl phosphine (PPr$_3$) in toluene. These mixtures were then each added to, and mixed with, separate quantities of the PHT. The resulting mixtures were filtered and rinsed with isopentane to remove the toluene. The resulting products were then dried in vacuo resulting in dry powder nickel-containing compositions.

A propene feed containing 10 volume % propene in 90 volume % isopentane was passed over the above described compositions. The pressure of the reactor was held in the range of from about 290 to about 310 psi. Results obtained are summarized in Table I below.

TABLE I

| Additive | Temperature | Time On Stream (hrs) | LHSV | Propene Conversion (wt. %) | Amount of Hexenes in conversion product (wt. %) | Amount of DMB in Hexenes (wt. %) |
| --- | --- | --- | --- | --- | --- | --- |
| PPh$_3$ | 40 | 5 | 1 | 80% | 65% | 36% |
|  | 40 | 6 | 2 | 76% | 81% | 39% |
|  | 40 | 10 | 2 | 72% | 85% | 39% |
| PPr$_3$ | 40 | 1 | 1 | 96% | 63% | 67% |
|  | 40 | 4 | 1 | 93% | 74% | 67% |
|  | 40 | 5 | 2 | 89% | 77% | 67% |
|  | 40 | 10 | 2 | 91% | 91% | 67% |
|  | 60 | 11 | 1 | 86% | 86% | 66% |
|  | 60 | 14 | 1 | 80% | 78% | 66% |

As shown in Table I above, the inventive catalysts are useful in the conversion of propene to hexenes, with good selectivity to the formation of dimethylbutenes (DMB). Regarding the phosphorous additive, the bulkier isopropyl groups lead to higher conversions and higher amounts of DMB as compared to the phenyl groups. Also, with increased LHSV the amount of hexanes produced (selectivity) increases.

Example II

A quantity of the following bis (salicylaldiminate) Ni (II) complex having the formula:

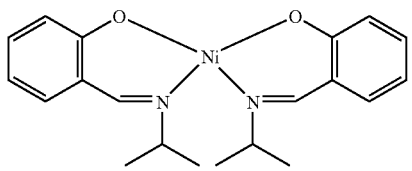

was mixed with tributyl phosphine ($PBu_3$) in toluene. This mixture was then added to, and mixed with, a quantity of the PHT. The resulting mixture was filtered and rinsed with isopentane to remove the toluene. The resulting product was then dried in vacuo resulting in a dry powder nickel-containing composition.

A propene feed containing 6 volume % propene in 94 volume % isopentane was passed over the above composition. Results obtained are summarized in Table II below.

TABLE II

| Additive | Temperature | Time On Stream (hrs) | LHSV | Propene Conversion (wt. %) | Amount of Hexenes in Conversion Product (wt. %) | Amount of DMB in Hexenes (wt. %) |
| --- | --- | --- | --- | --- | --- | --- |
| $PBu_3$ | 40 | 5 | 1 | 93% | 85% | 46% |
| | 50 | 10 | 1 | 93% | 84% | 44% |
| | 60 | 15 | 1 | 91% | 86% | 50% |
| | 40 | 16 | 2 | 87% | 87% | 50% |
| | 40 | 18 | 2 | 70% | 100% | 49% |

As shown in Table II above, the inventive catalyst is useful in the conversion of propene to hexenes, with good selectivity to the formation of dimethylbutenes (DMB). A higher LHSV (2 from 1) lowers the overall conversion to 70% from 93%, but with an increase in selectivity to hexenes from 85% to 100%.

While this invention has been described in detail for the purpose of illustration, it should not be construed as limited thereby but intended to cover all changes and modifications within the spirit and scope thereof.

That which is claimed:

1. A method comprising:
   a) mixing a phosphorous compound with a nickel complex comprising nickel bonded to a heteroatom, to thereby form a nickel-phosphorous-containing mixture; and
   b) contacting said nickel-phosphorus-containing mixture with a supported partially hydrolyzed alkylaluminum compound, thereby forming a nickel-containing composition that has an activity sufficient for at least 84% selectivity to hexenes in conversion of propene, wherein said nickel complex comprises at least one compound having the following structure:

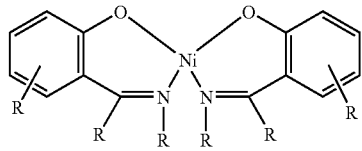

wherein:
R is selected from alkyl, aryl, alkenyl, hydrogen, and combinations thereof, any of which optionally can be partially oxidized or partially substituted by nitrogen-functional groups having the general formulas OH, OR, and $NH_yR_z$, respectively;
$y=3-z$; and
z ranges from 1 to 3.

2. The method of claim 1 wherein said nickel complex comprises the following compound:

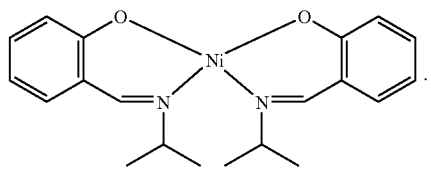

3. The method of claim 1 wherein said phosphorus compound has the formula $R_nPY_{3-n}$;
R is selected from alkyl, aryl, alkenyl, hydrogen, and combinations thereof, any of which optionally can be partially oxidized or partially substituted by nitrogen-functional groups having the general formulas OH, OR and $NH_yR_z$, respectively;
Y is selected from hydrogen and halogen;
$y=3-z$;
z ranges from 1 to 3, and
n ranges from 1 to 3.

4. The method of claim 1 wherein said phosphorous compound is selected from the group consisting of tributyl phosphine, triphenyl phosphine, triisopropyl phosphine, and combinations thereof.

5. The method of claim 1 wherein said supported partially hydrolyzed alkylaluminum compound is supported partially hydrolyzed trimethylaluminum.

6. The method of claim 1 wherein the support of said supported partially hydrolyzed alkylaluminum compound is silica.

7. The method of claim 1 wherein said method is performed at a temperature in the range of from about −20° C. to about 150° C.

8. The method of claim 1 wherein a solvent is added in step a); and wherein said solvent is removed in step b), thereby forming said nickel-containing composition.

9. The method of claim 8 wherein said solvent is toluene.

10. The method of claim 1, wherein the nickel-containing composition has an activity sufficient for conversion of at least 60 weight percent of propene to hexenes.

11. The method of claim 1, wherein the nickel-containing composition has an activity sufficient for 100% selectivity to hexenes in conversion of propene.

* * * * *